United States Patent [19]

Bocquet

[11] Patent Number: 4,767,763

[45] Date of Patent: Aug. 30, 1988

[54] COMPOSITION FOR ACHIEVING TUMOR REVERSION AND ITS USE IN CANCEROLOGY FOR DOGS

[76] Inventor: Roger L. E. Bocquet, 17 rue Chartran, 92200 Neuilly sur Seine, France

[21] Appl. No.: 883,300

[22] Filed: Jul. 7, 1986

Related U.S. Application Data

[63] Continuation of Ser. No. 694,898, Jan. 25, 1985, abandoned, which is a continuation of Ser. No. 458,906, Jan. 18, 1983, abandoned.

[30] Foreign Application Priority Data

Jan. 29, 1982 [FR] France .................. 82 01397

[51] Int. Cl.[4] ............... A61K 31/52; A61K 31/10; A61K 31/74
[52] U.S. Cl. .................. 514/264; 514/709; 424/78
[58] Field of Search ............... 514/264, 709; 424/78

[56] References Cited

PUBLICATIONS

Carter et al., Chemotherapy of Cancer, 2nd Ed., 1981, Wiley & Sons, N.Y., N.Y., pp. 26–43.
Chemical Abstracts, 93:197666w (1980).
Stock et al., Cancer Research, Supplement No. 2, 1955, pp. 179–187 and 321.

*Primary Examiner*—Jerome D. Goldberg
*Attorney, Agent, or Firm*—Young & Thompson

[57] ABSTRACT

Skin neoformations and sarcomas in dogs are treated with a composition containing by weight percent, in distilled water:

8–22% of polyethylene glycol having a molecular weight within the range of 1000 to 6000,
10–30% of dimethyl sulfoxide,
2.5–7.5% of theophylline.

2 Claims, No Drawings

COMPOSITION FOR ACHIEVING TUMOR REVERSION AND ITS USE IN CANCEROLOGY FOR DOGS

This application is a continuation of application Ser. No. 694,898, filed Jan. 25, 1985, now abandoned, which is a continuation of application Ser. No. 458,906, filed Jan. 18, 1983, now abandoned.

This invention relates to a composition for producing tumor reversion in dogs and to the use of this composition in cancerology in dogs.

Research workers have already devoted attention to tumor reversion for a long time and have been encouraged by the fact that spontaneous regression could occur in some types of cancer although such cases remained too rare.

Many authors have tried to use chemical drugs which might have reverting properties but without success.

However, on Feb. 27th, 1981, after several years of studies and experimentation on a wide range of potential revertants, I succeeded in achieving reversion of HeLa cells in vitro, not by using *one* revertant but by means of a revertant composition in which the complementary properties of its constituents were combined. This made it possible to overcome the disadvantage of the single drug which was not alone sufficient to induce the highly desirable process of reversion.

Tumor reversion was demonstrated by the reappearance of two well-known standard criteria in the field of cell culture, namely the reappearance of contact inhibition and the property of adhesion to glass.

It may be indeed be stated that this phenomenon is revolutionary inasmuch as reversion is accompanied by abandonment of uncontrolled proliferation and recovery of contact inhibition, this condition being none other than stoppage of proliferation when the cell layer in culture extends over the entire surface of the glass vessel, the bottom of which serves as a support for said layer.

Moreover, "normalization" of originally cancerous cells is also indicated by better adhesion of the cells either to each other or to the glass.

It is a well-known fact that cancer cells are readily detachable, and this is a major reason for the promotion of dissemination by metastasis.

Since the non-toxic revertant composition results in achievement and confirmation of these two properties, it was a logical procedure to study the potential application of the composition to the therapeutic field in dogs.

The composition is very easy to use and effectively inhibits tumor growth in dogs, thus enabling the rest of the body to utilize its own natural means (homeostatic but especially immunologic means) in order to eliminate cells which had previously been dangerous but have simply become useless.

In accordance with the invention, this composition is characterized by the association of three chemical products: polyethylene glycol, dimethyl sulfoxide and theophylline, as produced simply by mixing in distilled water.

When added to a culture of cancer cells in the surrounding culture medium (cells of cloned HeLa colonies, for example), this mixture initiates the appearance of tumor reversion.

The composition and the method of utilization of the composition will be more specifically described in the following non-limitative example.

DESCRIPTION OF EXPERIMENTS

A confluent layer of HeLa cells (cancer cells) in culture was treated in accordance with the invention.

The culture was prepared in a Falcon box having a surface area of 75 $cm^2$ and containing 30 ml of culture medium (MEM 2011 Eurobio) completed with 10% fetal calf-serum (SVF Eurobio).

First experiment—Basic experiment—The Reversion phenomenon

Flask No 1. The mixture prepared in the following proportions was added:
1.5 ml of a 10% solution of polyethylene glycol
0.5 ml of pure dimethyl sulfoxide
50 microliters of theophylline The medium was subsequently renewed twice at one-week intervals and in the proportions described above. Finally, the culture was renewed each week without any further addition of the revertant composition.

At the same time as this basic experiment, other flasks of the same type were put in competition.

Flask No 2. Reference flask without any addition for checking the normal cell growth in the HeLa culture in its usual medium.

Flask No 3. The only addition was polyethylene glycol (1.5 ml of the 10% solution).

Flask No 4. The only addition was pure dimethyl sulfoxide (0.5 ml).

Flask No 5. The only addition was 50 microliters of theophylline.

Flask No 6. The difference in this case was that polyethylene glycol (1.5 ml of the 10% solution) and pure dimethyl sulfoxide (0.5 ml) were added without theophylline.

Results

Flask No 1. Eight days after the instant of time 0, it was already possible to distinguish a regularly ordered pattern of cells which remained attached to the glass whereas in other locations the highly disordered state of the original cells continued to exist.

But as further renewals of the medium took place at intervals, so the process which had started continued until it was finally possible one month to six weeks later to obtain a strictly monolayer cell tissue extending over the entire surface of the flask after the non-reverted cells had been successfully eliminated, thrust aside, detached and veritably sapped by the normal cells.

Flask No 2. After three weeks, the culture of HeLa cells became detached and the cells passed into a state of suspension as may commonly be observed in this type of culture.

Flask No 3. The addition of polyethylene glycol had produced no change in the culture which had followed the growth process of Flask No 2.

Flask No 4. The addition of dimethyl sulfoxide had produced no change in the culture which had followed the growth process of Flask No 2 and No 3.

Flask No 5. The addition of theophylline had not produced any change in the culture which had followed the growth process of Flasks No 2, No 3 and No 4.

Flask No 6. In this flask, however, there could be observed after eight days zones of cells which had apparently undergone a reversion process in a regularly ordered pattern: these cells had remained attached to the glass in the midst of a tissue layer which was apparently in a disordered state.

However, as further renewals of the medium took place, so the process which had started did not seem to continue. Six weeks later, the appearance of the culture had remained in the same state (designated as a quiescent state) without obtaining a mat layer extending over the entire surface of the flask.

One important property is nevertheless worthy of note, namely the fact that the cells of the culture remained in place whereas, in the reference flask and during the same period of time, all the cells had already been in suspension for three weeks.

After six weeks, although the experiment had been completed, Flask No 1 was kept. Eighteen months later, however, it was again found that the reverted cell culture had remained in the same state or so-called quiescent state, in the form of a monolayer, and limited to the edges of the flask.

Second experiment—Competition between HeLa cells and reverted cells

During the basic experimentation, HeLa cell layers other than the reference HeLa cell layer had been simply preserved in order to maintain the culture strain in a continuous clone.

There had actually taken place an accidental "contamination" by cells which had undergone reversion on one of these cell layers. There then occurred a veritable cell inoculation (similar to germ inoculation) and scattered colonies in the form of speckled zones appeared ten to fifteen days later.

These colonies then began to take possession of the bottom of the flask and to sap the culture. They increased in size, thus forming circles or disks of strictly monolayer cell culture which met each other and became confluent, thus exerting a forward thrust on the HeLa cell layer and giving rise at the time of contact to the formation of a bulge resembling a lip.

The HeLa cell layer soon became a network pattern (like a wire-mesh fence). The HeLa cells were finally destroyed, torn apart, disorganized, and then passed into suspension one after the other. There then remained only a tissue of reverted cells in a single layer limited to the edges of the flask.

This experiment leads to the conclusion that the reverted cells exhibit much stronger adhesion to the glass and a vitality which is superior to HeLa cells in culture (as has subsequently been verified by the fact that trypsination of these cells is more difficult to carry out).

As a result of this experiment which was performed without having been projected, the tissue layer or mat of reverted cells forming a colony over the entire bottom of the flask had observed contact inhibition. It then remained in the quiescent state and has continued to remain in this state for the last sixteen months.

Third experiment—Maintenance of the quiescent state

One of the flasks containing reverted cells in the quiescent state had been left unattended for a four-week period. Eight months after the instant 0, a certain number of reverted cells were found to be dead, detached and in suspension, thus leaving holes in the tissue layer or mat of cells. Moreover, the culture medium had become acid. After rinsing and renewal, the mat layer was completely reconstituted and the culture again acquired its previous quiescent appearance. Eighteen months after the instant 0, the layer was still in the same state.

Fourth experiment—Demonstration of the hereditary character of reappearance of contact inhibition At the instant 0, one of the flasks containing reverted cells in the quiescent state was trypsinated in order to carry out a first "passage" (this term being intended to designate an operation which is identical with bacteriological subculture).

The culture formed without any difficulty a new monolayer mat which became quiescent as soon as it reached the edges of the flask.

A second passage was performed 23 days after (total period: d. 23)

A third passage was performed 26 days after (total period: d. 49)

A fourth passage was performed 25 days after (total period: d. 74)

Finally, a fifth and last passage was performed 16 days after (total period: d. 90).

At the end of five passages, the experiment had taken place over a total period of 90 days and the experimental conditions amply demonstrated a constancy of reproduction of the phenomenon. The experiment was discontinued after it had been considered as a proven fact that a continuous cloned colony had been established and that the reverted HeLa cells had acquired a hereditary character.

It has since become possible to make permanent use of the reverted cells in exactly the same manner as the cells of a new continuous cloned colony for other laboratory requirements.

Fifth Experiment—Demonstration of the independance of recovery of the culture (starting from the quiescent state) with respect to time In order to ensure that this final experiment should be demonstrative, recourse was had to a flask of reverted cells in quiescent culture and having an age of eighteen months.

After trypsination, these inoculated cells colonized the new flask. A successful sequence of three passages was even carried out by way of confirmation.

Experimental demonstration of tumor reversion had been achieved. This demonstration was due neither to chance nor to an artifact. Furthermore, reproducibility was an established fact.

In summary, the experiments hereinabove described demonstrate that:

The revertant composition produces action on the HeLa cells in culture and results in tumor reversion in dogs.

This reversion is characterized by the reappearance of essential properties which had disappeared as a result of cancerous transformation and among which the following properties have been identified: contact inhibition, stronger adhesion to glass and better cohesion between the constituent cells of the cell tissue.

It has been clearly shown that contact inhibition in particular was maintained as new mitoses took place, that this property was therefore transmitted in a hereditary manner in successive generations, and that it was independent of the time of recovery of the culture and of the length of the quiescent periods.

As has also been clearly shown, it was essential to associate at least two constituents, namely polyethylene glycol and dimethyl sulfoxide, but also to add theophylline which endows the reversion process with its full value and effect.

In consequence, the reverting action of the composition is dependent on the association of a membrane modifier consisting of polyethylene glycol (whose molecular weight of 1000 to 6000 is indifferent) and of a revertant consisting of dimethyl sulfoxide to which is added an adjuvant, namely theophylline.

The proportions indicated in the first experiment constitute a basis and a mean value.

Complementary experiments have served to establish that:

1. The proportion of atoxic membrane modifier (polyethylene glycol) can be affected only by the limits of its viscosity, its optimum proportion being 15% (±7%) in solution in distilled water.

2. The proportion of practically atoxic basic revertant (dimethyl sulfoxide) can be substantially increased. This compound does not have any limit of viscosity since it is well-known that its diffusion rate is incredibly high. This proportion can therefore be readily fixed at 20% (±10%) of the volume of the solution but an increase in proportion is not ipso facto an advantage to be sought systematically.

3. On the other hand, the proportion of theophylline must be kept within a fairly narrow range. A proportion of theophylline fixed at 50 microliters per 30 ml of medium is an experimental standard from which it would be advisable not to stray too far by consequently keeping to a proportion of 5% (±2.5%) of the solution.

Extension of the application of the invention from the "in vitro" field to the "in vivo" field After the results obtained and verified in vitro, it is logical to contemplate utilization in the therapeutic field as an anti-cancer drug.

This application must be based on two information series:

(1) Toxicologic information
(2) Clinical experimentation

In order to substantiate the potential pharmaceutical use of the invention on an industrial scale, these two points will be dealt with successively.

(1) Toxicologic information (a) Polyethylene glycol is a neutral chemical compound which is completely free of any toxicity, which has already been employed in subcutaneous or intravenous injections, and which has never had any immediate (allergic) effect or secondary effect either in animals or in human beings.

(b) Dimethyl sulfoxide $C_2H_6SO$ has formed the subject of very extensive and highly varied clinical studies both in animals as a result of toxicologic studies on a certain number of animal species.

All these researches and studies have been published in a 671-page report published on Mar. 15th, 1967 in the Annual Transactions of the Science Academy of New York (vol. No 141, Art. 1, p. 1–671).

But this chemical compound is not mentioned at any time as a revertant.

Moreover, these studies have brought out the fact that dimethyl sulfoxide is free of any toxicity.

(c) Theophylline $C_7H_8N_4O_2$ (dimethyl-1,3 xanthine) is a chemical compound which has been employed as a drug for many years. It is a diuretic, heart stimulant and bronchial vasodilator which is used in particular for attacks of asthma.

So far as these three constituents are concerned, it will therefore serve no useful purpose to make a further toxicologic study in extenso.

However, the following DL50's may be mentioned:
Polyethylene glycol

In the case of rats, the DL50 of polyethylene glycol (600) is 7.8 grams/kg. Transposed to human beings (having a weight of approximately 70 kg), this would constitute a dose of 546 grams whereas the dose which is considered sufficient represents a proportion of only 1/546 of this DL50.

Dimethyl sulfoxide

The DL50 of dimethyl sulfoxide is 12 grams/kg in the case of mice and is 20.5 grams/kg in the case of rats. This is low systemic toxicity which produces the same manifestations in all species.

By comparison, the dose used in human beings in a single injection represents a proportion of 1/1050 of this DL50.

Theophylline

The DL50 of theophylline is 400 mg/kg in the case of mice and is 300 mg/kg in the case of rats.

These values are high.

If, by comparison, these doses are related to the maximum therapeutic dose employed in human subjects, that is, 0.02 gram of pure theophylline for a single injection of 10 ml of product, this dose represents a proportion of only 1/1225 of the mean DL50 of 350 mg/kg.

(2) Clinical experimentation

Although this experimentation has been of a very summary nature up to the present time, it nevertheless permits a record of the following important observations obtained after a series of subcutaneous injections spaced in principle at intervals of eight days at a rate of 10 ml at each injection of the following mixture:

Distilled water: 90 ml
Polyethylene glycol: 9 grams
Pure dimethyl sulfoxide: 9 ml
Theophylline: 3 ml of the ordinary 6% pharmaceutical solution.

The following effects were produced:

withering, drying-up and 90% disappearance of a skin neoformation (small secondary white tumor, smooth-walled and hairless) after three injections spaced at exceptional intervals of only four to five days.

transformation of the principal tumor in the same animal: a large-size sarcoma of the subocular face which had become fluctuating followed by purulent fusion and external discharge like a cold abcess, after ten injections performed at eight-day intervals starting from the third injection.

In conclusion:

After presenting the characteristics of a revertant composition in vitro, it is undeniable that the composition in accordance with the invention therefore retains the same characteristics in vivo in dogs.

However, a model prepared for experimentation in vitro has to be adapted to the in vivo field in dogs.

With this objective, the distilled water is replaced by physiological serum or by Quinton serum.

Moreover, it seems a well-established fact that the dilution ranges of polyethylene glycol and of dimethyl sulfoxide are effective. It proves necessary on the other hand to adapt the dog's body to the action of theophylline (known in its usual pharmaceutical presentation as a 6% solution) by effecting an approximate dilution for the first injections with doses reduced to 1/50 and to 1/100 of those already defined and which will be administered thereafter.

What is claimed is:

1. A composition for treating skin neoformations and sarcomas in dogs, containing by weight percent, in distilled water:
   8–22% of polyethylene glycol having a molecular weight within the range of 1000 to 6000,
   10–30% of dimethyl sulfoxide,
   2.5–7.5% of theophylline.

2. A method of treating skin neoformations and sarcomas in dogs, comprising administering to a dog in need of the same an effective amount of a composition containing, by weight percent, in distilled water:
   8–22% of polyethylene glycol having a molecular weight within the range of 1000 to 6000,
   10–30% of dimethyl sulfoxide,
   2.5–7.5% of theophylline,
said amount being effective to treat skin neoformations and sarcomas.